United States Patent [19]

Lynn et al.

[11] Patent Number: 4,673,397
[45] Date of Patent: Jun. 16, 1987

[54] SPLASH BACK REDUCTION DRIP CHAMBER

[75] Inventors: Kenneth M. Lynn, Spring Grove; Richard Rollins, Mundelein, both of Ill.

[73] Assignee: Baxter Travenol Laboratories, Inc., Deerfield, Ill.

[21] Appl. No.: 926,802

[22] Filed: Oct. 29, 1986

Related U.S. Application Data

[63] Continuation of Ser. No. 763,302, Aug. 2, 1985, abandoned, which is a continuation of Ser. No. 512,796, Jul. 11, 1983.

[51] Int. Cl.⁴ .............................................. A61M 5/16
[52] U.S. Cl. .................................................... 604/251
[58] Field of Search ................................. 604/251–256

[56] References Cited

U.S. PATENT DOCUMENTS

| | | | |
|---|---|---|---|
| 3,563,090 | 2/1971 | Deltour | 73/194 |
| 3,596,515 | 8/1971 | Cramer | 73/194 R |
| 3,774,603 | 11/1973 | McPhea | 73/327 |
| 4,314,484 | 2/1982 | Bowman | 73/861.41 |
| 4,328,801 | 5/1982 | Marx et al. | 604/253 X |

Primary Examiner—Stephen C. Pellegrino
Attorney, Agent, or Firm—Paul C. Flattery; Kay H. Pierce

[57] ABSTRACT

A medical fluid administration set and a drip chamber (10) for use on the administration set are disclosed. The drip chamber (10) may be used with conventionally available drop counters whereby fluid flow can be monitored. The drip chamber (10) is intended for incorporation into a medical fluid administration set. At least a portion of the inside surface of the drip chamber (10) has a matte or satin finish (20) as distinguished from a glossy finish. The matte finish (20) alters the surface characteristics between solution residing in the drip chamber (10) and the drip chamber (10) itself, thereby preventing substantial upward splash back or bounce back of liquid drops impacting the surface of the fluid in the drip chamber (10) which splash back or bounce back can result in erroneous flow rate indications.

16 Claims, 4 Drawing Figures

SPLASH BACK REDUCTION DRIP CHAMBER

This application is a continuation of application Ser. No. 763,302, filed Aug. 2, 1985, now abandoned, which is a continuation of application Ser. No. 512,796, filed July 11, 1983.

FIELD OF THE INVENTION

This invention generally relates to drip chambers suitable for use in-line on medical fluid administration sets. Often, the drip chamber is connected to the outlet of a burette. Alternatively, the drip chamber may be connected to the outlet of a container, for example, a glass bottle or flexible plastic container, containing parenteral liquid, blood, or any of the myriad of liquids intended to be administered to patients. Typically, the drip chamber includes an inlet intended to be connected to a drop former and a plastic chamber. The inlet of the drip chamber communicates with the inside of the plastic chamber via the drop former. The specific province of this invention resides in a drip chamber which reduces splash back of liquid solution droplets impacting liquid residing in the chamber bottom. A drip chamber having this characteristic is particularly useful when liquid drops are counted by electronic drop counters.

BACKGROUND OF THE INVENTION

There exists a variety of designs for tubing administration sets for delivering medical liquids or solutions to patients. These administration sets vary widely in their particular uses and designs. Drip chambers often are included, in-line, in fluid administration sets. Principal functions of the drip chambers, among others, are to assist in priming the administration set in order to commence the flow of liquid to the patient and to permit medical personnel to determine the flow rate of the fluid through the administration set by counting the number of falling drops in a given period of time.

Electronic drop counting devices have been designed to be used in conjunction with administration sets and drip chambers for situations where long term monitoring of solution infusion rate is necessary or desirable. Drop counting devices typically function by using a light source and a photoreceptor having associated electronic circuitry. Drops of fluid entering the drip chamber will interrupt the light beam directed to the photoreceptor causing changes in the electronic circuitry. Individual drops of liquid may be counted in this manner. Flow rates can be calculated by electronically monitoring the number of drops in a given period of time and using known drop volumes for particular fluids.

Conventionally available fluid administration sets are sold having drip chambers of various shapes and sizes, but all of the drip chambers can suffer from a significant shortcoming which can result in erroneous fluid flow rate calculation. Erroneous flow rate readings predominently are caused by fluid splash back or fluid bounce back.

More precisely, in conventional drip chambers, a certain volume of fluid resides in the bottom portion of the drip chamber. Fluid exiting the drip chamber typically is replaced at a rate greater than or equal to the rate of fluid entering the drip chamber. Fluid droplets striking the surface of this retained fluid can be reflected back upward in the direction of their fall, namely, the principal droplets entering the chamber appear to be reflected back upward. Not wishing to be limited to any theory of operation, it appears that the mechanism of splash back is rather like a falling body bouncing on a trampoline. Principal droplets should be distinguished from dispersed droplets caused by the impact of the entering principal droplets. Principal drops or droplets are defined as fluid drops entering the drip chamber after being formed in a drop former. This fluid splash back or bounce back can result in erroneous flow rate readings. Often, these upwardly redirected principal fluid droplets again will be detected by the electronic drop counter and register as another drop of fluid entering the drip chamber. It is believed that the surface tension or surface energy characteristics of both the fluid and the interior surfaces of the drip chamber effect this fluid splash back or bounce back.

It would be advantageous to reduce or substantially eliminate splash back or bounce back in a drip chamber thereby avoiding erroneous indications of fluid flow.

It would be expedient to provide a drip chamber having surface tension or surface energy characteristics such that the phenomenon of droplet splash back or bounce back was eliminated.

Also, it would be expedient to have an administration set for use with a drop counter whereby erroneous indication of fluid flow by a drop counter would be eliminated or greatly reduced as a source of error.

DESCRIPTION OF THE INVENTION

A medical fluid administration set and a drip chamber for use on the administration set constitute this invention. The drip chamber of this invention may comprise a drip chamber of known configuration, for example, the drip chamber included in the 2C1035 BURETROL ® Volumetric Pump Administration set sold by Travenol Laboratories, Inc., Deerfield, Ill. At least a portion of the inside surface of the drip chamber has a circumferential band textured to a matte or satin finish. This circumferential band of matte finish can be described as a zone of matte finish which is intended to be adjacent to the anticipated surface of the liquid in the chamber. While theoretical reasons are uncertain, it is believed that contact of the liquid with the matte finish, especially adjacent the liquid surface, supresses upward splash back, in which a droplet is propelled upwardly from the liquid surface in reaction to a drop falling into the liquid surface.

The term "matte finish" is intended to describe a surface having irregularities, typically peaks and valleys, having transverse dimensions on the order of 30 to 600 microns, for example, and heights from the peak to the valley of typically 30 to 600 microns, to provide a surface that has a visibly milky cast, in contrast to the optical clarity of a smooth, glossy finish. Dimensions other than those described above also may be used in the matte finishes used in this invention.

It is contemplated that the drip chamber of this invention may be used with conventionally available drop counters whereby fluid flow can be monitored. Also, it is contemplated that the drip chamber of this invention may be incorporated into medical fluid administration sets.

A preferred embodiment drip chamber is the configuration currently used on the above-referenced Travenol Laboratories, Inc., product. A preferred drip chamber of this invention comprises a flexible chamber formed of polyvinyl chloride thermoplastic material having a thickness of about 0.03 inch to 0.08 inch. The preferred polyvinyl chloride thermoplastic material is a clear, flexible thermoplastic manufactured by Alpha Plastics and Chemicals and designated as polyvinyl chloride thermoplastic number 3006/1-85. Other materials having similar properties may be used. For example, the drip chambers may be made from polyolefin thermoplastics such as polypropylene, polyester and nylon thermoplastics, and polyurethanes. Choice of material for the drip chamber should take into consideration the need for the drip chamber to be transparent to the light used in conventionally available drop counters. Drip chambers having other configurations, however, may take advantage of the particular benefits achieved by the present invention.

In a preferred embodiment of the drip chamber, at least a portion of the interior surface of the drip chamber has a substantially circumferential band of matte or satin finish as distinguished from a glossy finish. The circumferential band of matte finish preferably is adjacent the anticipated liquid surface level. A fluid level line, defined by an area of glossy finish, may interrupt the matte or satin finish so that the matte finish is above and below the fluid level line. The fluid level line functions as target point which indicates a desired level of fluid. It is positioned so that personnel priming a set having the drip chamber, can maintain fluid level below the sensing region of a drop counter used therewith. It may be desirable for most of the inside surface of the drip chamber to have a matte finish, bearing in mind that a portion of the drip chamber in communication with a drop counter, which uses a light source and photoreceptor, must be of sufficient optical clarity to allow proper functioning of the drop counter.

Generally, the surface irregularities—typically peaks and valleys—defining the matte finish have heights from the peak to the valley of between about 30 to 600 microns. Preferably, the heights from the peak to the valley are between about 140 to 230 microns.

The matte or satin finish on the interior surface of the drip chamber may be produced using conventionally known techniques. For example, the glossy interior surface of a drip chamber can be subjected to shot blasting techniques or chemical etching to produce the matte finish. Also, mold core pins, used with the molds for manufacturing the drip chambers, can have their exterior surfaces acid etched, sand blasted, embossed, electrical discharge machined, or hand engraved. A mold core pin having a portion of its exterior surface so treated will impart a satin or matte finish to a portion of the interior surface of the drip chamber.

The medical solution administration set of this invention is comprised of a conduit line having a spike at one end for accessing solution in a container and having an adapter at its other end for connecting to various patient access devices. A drip chamber, which reduces splash back or bounce back of principal fluid drops, is included as one of the medical devices in flow communication with the conduit of the administration set.

A preferred embodiment of the fluid administration set of the present invention comprises flexible tubing connecting the various elements of the administration set in flow communication in the following order: a hollow spike for accessing a container of medical fluid; a burette chamber having a drop former at its outlet; a drip chamber communicating at its inlet with the drop former of the burette chamber, the drip chamber having a matte finish on at least a portion of the bottom half of its inside surface but not interfering with the normal functioning of a drop counter; an injection site; a casette for use with an infusion pump; two more injection sites; and, an adapter designed for communicating with various patient access devices at the other end of the administration set. Additional ancillary clamps, injection sites, or the like, may be added to the administration set. Also, the invention is not limited to an administration set having all of the preferred devices in addition to the drip chamber thereon.

A benefit of the present invention is that upward splash back or bounce back of principal liquid drops dropping into the drip chamber is eliminated or greatly reduced, thereby minimizing the chances of erroneous flow rate indications as monitored by a drop counter.

Another benefit achieved by the present invention is that an administration set having a drip chamber of the present design in flow communication with the flexible tubing of the administration set can be used more confidently by medical personnel since erroneous indications of fluid flow rate caused by upward splash back or bounce back is eliminated or greatly reduced.

BRIEF DESCRIPTION OF THE DRAWINGS

For a more complete understanding of this invention, reference should now be had to the embodiments illustrated in greater detail in the accompanying drawings.

In the drawings.

DETAILED DESCRIPTION OF THE DRAWINGS

Figure 1:
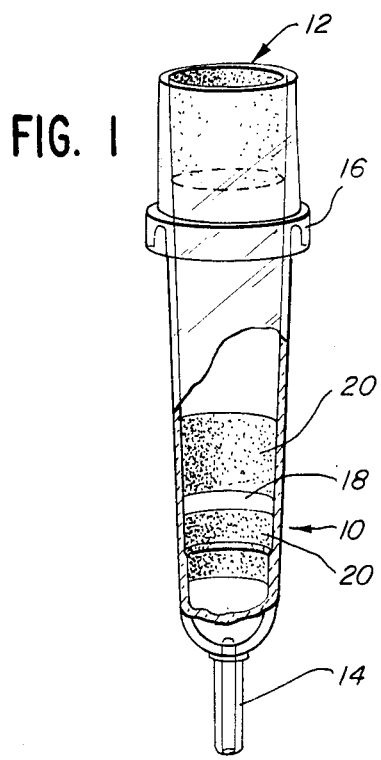
FIG. 1 is a perspective view of the drip chamber of the present invention, partially cut away, illustrating the matte or satin finish on at least a portion of the interior surface of the drip chamber.

Turning now to the drawings, FIG. 1 illustrates drip chamber 10. Drip chamber 10 has inlet 12 and outlet 14. Drip chamber 10 preferably is made from polyvinyl chloride thermoplastic material having a thickness of about 0.03 inch to 0.08 inch. Drip chamber 10 is of generally circular cross section having inside diameters ranging from about 0.55 inch to 0.65 inch at inlet 12 to 0.070 inch to 0.090 inch at outlet 14. Polyvinyl chloride thermoplastic material is the preferred material, however, other suitable materials may be used. For example polyolefin materials such as polypropylene may be used and nylon, polyester and polyurethane materials also may be used.

As illustrated in FIG. 1, drip chamber 10 also has shoulder stop or lip 16. Shoulder stop 16 functions to align and fix drip chamber 10 in conventionally available drop counters, for example, the Travenol FLO-GARD TM 8000 drop counter manufactured by Oximetrix, Inc., of California. At least a portion of the interior surface of drip chamber 10 has area 20 defined as a circumferential band textured in a matte or satin finish. Matte finish area 20 is intended to be adjacent to the anticipated surface of the liquid in drip chamber 10. The remainder of the finish on the interior surface generally and preferably is a glossy finish.

Circumferential fluid level line 18 interrupts a portion of matte finish area 20 and is defined as an area of glossy finish. Fluid level line 18 functions as a target point which indicates a desired level of fluid. It is positioned so that personnel priming an administration set having the drip chamber can maintain fluid level below the sensing region of the drop counter.

Matte finish area 20 on interior surface of drip chamber 10 can be formed by a number of conventional methods. Generally, the surface irregularities defining the matte finish area 20 have heights from the peak to the valley of between about 30 to 600 microns. Preferably, the heights from the peak to the valley are between about 140 to 230 microns.

Matte finish area 20 may be formed by shotblasting or chemically etching the interior surface of drip chamber 10 or by altering the exterior surface characteristics of the mold core pin of the mold used to form drip chamber 10. For example, the mold core pins can have at least a portion of their exterior surfaces acid etched, sand blasted, electrical discharge machined, or hand etched. A mold core pin having its exterior surface so treated will impart a satin or matte finish to the interior surface of the drip chamber. It is preferred that matte finish 20 be formed by altering the characteristics of the exterior surface of the mold core pins. It is preferred that matte finish 20 be formed in a mold whose mold core pin has had its exterior surface acid etched to AF-300 finish conventionally performed by Comet Die Company of Chicago, Ill.

Figure 2:
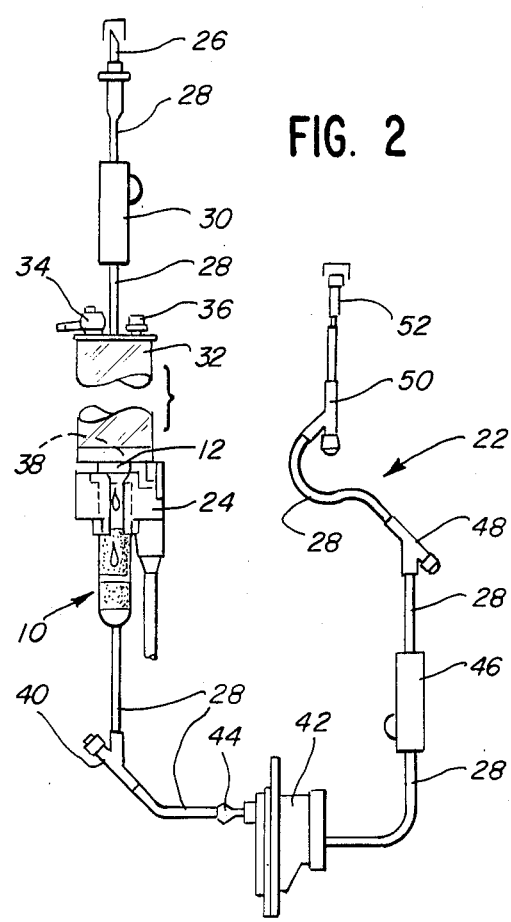
FIG. 2 is a plan view illustrating an administration set having, as an element, a drip chamber of the present invention.

An administration set of the invention of the present application is illustrated in FIG. 2. Administration set 22 is shown with drop counter 24 mounted around drip chamber 10. Administration set 22 is comprised of spike connector 26 for accessing containers of medical fluids, parenteral solutions or the like. Flexible tubing 28 connects various elements of fluid administration set 22 in flow communication. On-off, roller clamp 30 is carried on tubing 28 between spike 26 and burette chamber 32. Burette chamber 32 is illustrated with airway control lever 34 and injection site 36. A drop former 38 resides in the bottom of burette chamber 32 and forms drops of solution. Drip chamber 10 has inlet 12 accessing the outlet of burette chamber 32. Injection site 40 is found between drip chamber 10 and pump casette 42. Pump casette 42 has plunger 44 residing thereon.

The final portion of administration set 22 has roller clamp 46 residing on tubing 28 and injection sites 48, 50 further downstream. Administration set 22 terminates in adapter 52 intended for communicating with various patient access devices. It should be appreciated, of course, that drip chamber 10 may reside on a tubing administration set similar to administration set 22 described hereinabove or on tubing administration sets having more or fewer elements as part of the administration set general structure.

Figure 3:
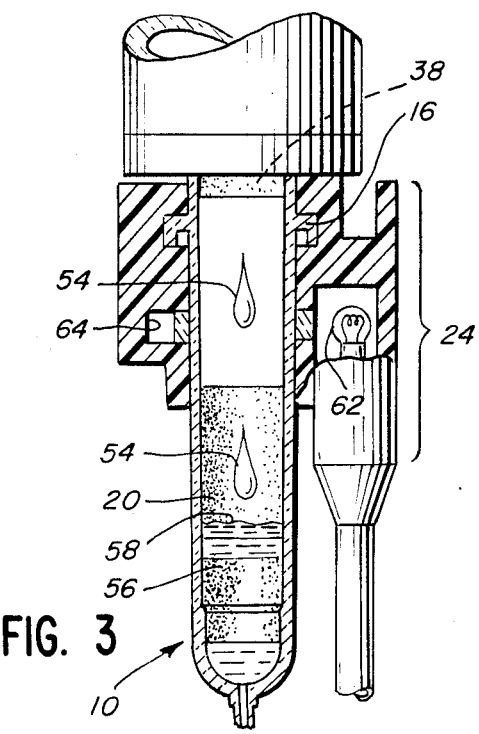
FIG. 3 is a partial plan view showing the falling fluid drops in a drip chamber having a matte finish on its interior surface.

FIG. 3 is illustrative of the effect that matte finish area 20 has on principal drops 54 striking fluid 56 residing in the bottom portion of drip chamber 10. Principal drops are defined as fluid drops entering drip chamber 10 after being formed in drop former 38.

Upward drop splash back or bounce back of principal drops 54 is minimal or nonexistent when drops 54 strike surface 58 of liquid 56. There may, however, be some splashing of dispersed droplets caused by the impact of the entering principal drops. Drop counter 24 is shown attached to drip chamber 10 and fixed by shoulder 16. Drop counter 24 has light source 62 and photoreceptor 64. Principal droplets 54 interrupt light passing from light source 62 to photoreceptor 64 and are detected as one drop. Known volumes for drops of particular fluids can be used to calculate flow rates from the number of drops counted by drop counter 24 in a given time period. It is believed that the surface tension or surface energy characteristics of drip chamber 10 are effected by matte finish area 20 thereby inhibiting or eliminating droplet bounce back or splash back. As is shown in FIG. 4, the droplets splashing back upward (Again, not wishing to be limited to any theory of operation, it appears that the mechanism of splash back is rather like a falling body bouncing on a trampoline) are detected by drop counter 24 which can result in erroneous indications of flow rate.

Figure 4:
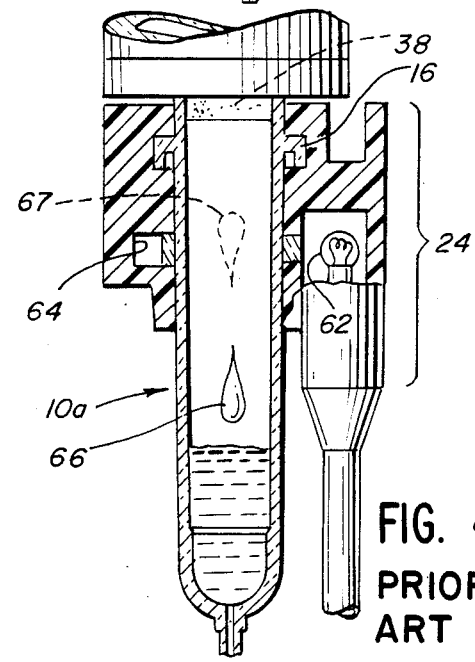
FIG. 4 is a partial plan view of a prior art drip chamber showing drops of fluid falling therein.

FIG. 4 illustrates a prior art drip chamber 10a, substantially similar to drip chamber 10 except for the differences hereinafter noted. Drip chamber 10a does not have a matte finish area on its interior surface. Drip chamber 10a is shown with drop counter 24 thereon and therearound and held in a fixed position on shoulder 16. Drop counter 24 has light source 62 and photoreceptor 64. Principal drops of solution 66 entering drip chamber 10a interrupt a light beam from light source 62 to photoreceptor 64 and are counted as a drop. Flow rate measurements can be made by calculating the drop rate and using the known volume of a drop of the solution. Substantial upward splash back or bounce back of principal drops of solution is shown. Principal droplet 67 (shown in phantom) has rebounded or splashed back upward. Droplet 67 also is detected by drop counter 24 and registers as an additional drop of fluid entering drip chamber 10a. This can result in erroneous indications of flow rate, and depending on the drop counter unit, can actuate alarms, shut off flow or both.

The above has been offered for illustrative purposes and is not intended to limit the invention of this application which is defined in the claims below.

What is claimed is:

1. A drip chamber defining a flexible plastic chamber having an interior surface, an inlet for communicating with drop former, and an outlet, the improvement comprising:
    splash back reduction means for reducing splash back of droplets in said chamber, said means including an irregular finish on at least a portion of said interior surface substantially adjacent an anticipated liquid surface level in said chamber, said irregular finish having peaks and valleys ranging from about 140 to 240 microns width, the heights from peaks to valleys ranging from about 140 to 240 microns.

2. The drip chamber of claim 1 wherein portions of said interior surface have substantially circumferential bands of matter irregular finish above and below said anticipated liquid surface level.

3. The drip chamber of claim 2 wherein said drip chamber is made from a polyvinyl chloride material.

4. The drip chamber of claim 2 wherein said chamber has a length of about 1.75 inches to 3.5 inches, an inside diameter at its inlet of about 0.55 inch to 0.65 inch, and an inside diameter at said outlet of about 0.070 inch to 0.090 inch; and said chamber being formed of a polyvinyl chloride thermoplastic material; said polyvinyl chloride thermoplastic material having a thickness of about 0.03 inch to 0.08 inch.

5. An administration tubing set for delivering medical fluids to a patient, said set having conduit means to maintain components in flow communication and arranged along the conduit means in the following order: spike means for accessing a container, a drip chamber having an interior surface, the administration set terminating in connector means for connecting to patient access devices, the improvement comprising:

splash back reduction means for reducing splash back of droplets in said chamber, said means including an irregular finish on at least a portion of said interior surface adjacent an anticipated liquid surface level in said chamber said irregular finish having peaks and valleys ranging from about 140 to 240 microns width, the heights from peaks to valleys ranging from about 140 to 240 microns.

6. The administration tubing set of claim 5 wherein at least a portion of the bottom half of the interior surface of said drip chamber has a substantially circumferential band of irregular finish thereon.

7. The administration tubing set of claim 5 wherein portions of the interior surface of said drip chamber have substantially circumferential bands of irregular finish above and below said anticipated liquid surface level.

8. The administration tubing set of claim 5 wherein said drip chamber is made from a polyvinyl chloride material.

9. A method for improving the accuracy of a drop counting device, said drop counting device being used to count drops of a liquid as the drops fall into a chamber, said chamber having a liquid in the bottom of the chamber, said method comprising the steps of: dropping liquid drops into said chamber, and reducing splash back of drops impacting the liquid in the bottom of the chamber, wherein said splash back reduction step includes providing at least a portion of the inside surface of the chamber with an irregular finish, said portion being adjacent an anticipated surface level of the liquid chamber, said portion having peaks and valleys ranging from about 140 to 240 microns, the height from peaks to valleys ranging from about 140 to 240 microns, said irregular finish being adjacent an expected liquid surface level.

10. A drip chamber defining a flexible plastic chamber, an inlet for communicating with a drop former, and an outlet, the improvement comprising:

said drip chamber with at least a portion of its interior surface having a substantially circumferential band of irregular finish thereon, said irregular finish including peaks and valleys on the order of about 170 to 240 microns width, the heights from the peaks to the valleys being on the order of about 170 to 240 microns, said circumferential band being adjacent the anticipated liquid surface level.

11. The drip chamber of claim 10 wherein at least a portion of the bottom half of its interior surface has said circumferential band of irregular finish thereon.

12. The drip chamber of claim 10 wherein portions of its interior surface have substantially circumferential bands of irregular finish above and below said anticipated liquid surface level.

13. The drip chamber of claim 10 wherein said drip chamber is made from a polyvinyl chloride material.

14. The drip chamber of claim 10 wherein said chamber has a length of about 1.75 inches to 3.5 inches, an inside diameter at its inlet of about 0.55 inch to 0.65 inch, and an inside diameter at said outlet of about 0.070 to 0.090 inch; and said chamber being formed of a polyvinyl chloride thermoplastic material; said polyvinyl chloride thermoplastic material having a thickness of about 0.03 inch to 0.08 inch.

15. An administration tubing set for delivering medical fluids to a patient, said set having conduit means to maintain components in flow communication and arranged along the conduit means in the following order: spike means for accessing a container, a drip chamber, the adminstration set terminating in connector means for connecting to patient access devices, the improvement comprising:

said drip chamber with at least a portion of its interior surface having a substantially circumferential band of irregular finish thereon, said irregular finish including peaks and valley on the order of about 140 to 230 microns width, the heights from the peaks to the valleys being on the order of about 140 to 230 microns, said circumferential band being adjacent the anticipated liquid surface level.

16. The administration tubing set of claim 15 having said drip chamber wherein at least a portion of the bottom half of the interior surface of said drip chamber has a circumferential band of irregular finish thereon.

* * * * *